United States Patent [19]

Wedel

[11] Patent Number: 4,898,178
[45] Date of Patent: Feb. 6, 1990

[54] MONOLITHIC DISPOSABLE NEEDLE GUIDE FOR ULTRASOUND TRANSDUCERS

[76] Inventor: Victor J. Wedel, P.O. Box Q, Kalona, Iowa 52247

[21] Appl. No.: 314,291

[22] Filed: Feb. 22, 1989

Related U.S. Application Data

[63] Continuation of Ser. No. 42,387, Apr. 24, 1987, abandoned.

[51] Int. Cl.$^4$ .................................................. A61B 8/00
[52] U.S. Cl. .............................. 128/662.05; 128/24 A; 128/754; 604/116
[58] Field of Search ....... 604/115, 116, 117, DIG. 26; 83/701; 128/662.05, 24 A, 754

[56] References Cited

U.S. PATENT DOCUMENTS

| | | | |
|---|---|---|---|
| 3,538,915 | 11/1970 | Frampton | 604/272 |
| 4,402,324 | 9/1983 | Lindgren et al. | 128/662.05 |
| 4,408,611 | 10/1983 | Enjoji | 604/116 X |
| 4,469,106 | 9/1984 | Harui | 128/660 |
| 4,491,137 | 1/1985 | Jingu | 128/660 |
| 4,497,325 | 2/1985 | Wedel | 604/116 X |
| 4,504,269 | 3/1985 | Durand | 604/272 |
| 4,542,747 | 9/1985 | Zurinski et al. | 128/660 |
| 4,635,644 | 1/1987 | Yagata | 128/660 |

OTHER PUBLICATIONS

Advanced Technology Laboratories, Inc., 8/1982, "Biopsy Guide".

Primary Examiner—Carl D. Price
Attorney, Agent, or Firm—Gregory G. Williams

[57] ABSTRACT

A needle guide system for use with an ultrasound transducer where a needle is inserted into a groove in a guide member which is attached to a sheath enclosed transducer with a mounting bracket.

5 Claims, 2 Drawing Sheets

MONOLITHIC DISPOSABLE NEEDLE GUIDE FOR ULTRASOUND TRANSDUCERS

This application is a continuation of application Ser. No. 07/042,387, filed Apr. 24 1987, now abandoned.

BACKGROUND OF THE INVENTION

This invention generally relates to the use of ultrasound transducers in conjunction with a needle, biopsy instrument, catheter or etc. in medical procedures, and more particularly may relate to the use of ultrasound transducers and scanners as an aid to physicians, such as, obstetricians when performing amniocentesis procedures, in a sterile clinical setting.

In recent years, there has been a ground swell of intense concern among medical and public health professionals relating to the spread of the acquired immune deficiency syndrome, commonly known as AIDS. Fervent debates rage on among top medical researchers about how the AIDS virus may be transmitted, but most prominent medical scholars agree that one way the AIDS virus may be transmitted is by the direct exchange that occurs in a blood to blood exchange. One possible direct exchange occurs when an unaffected person is the recipient of blood from a donor having AIDS, such as in a transfusion. However, this high volume of blood exchange is not necessary for transmission to occur. In fact, it is believed that the AIDS virus can be transmitted to another, when a needle which has been exposed to the virus is used by an unaffected person. For this reason, it is commonly believed that drug users, who share needles for drug injections, are in a high AIDS risk category. Similarly, pregnant women undergoing amniocentesis, with the aid of ultrasound transducers and their associated needle guides, both of which are used again and again on numerous women, are at an elevated risk because of the increased exposure of the needle to the previously used transducer and needle guide.

One needle guide which has enjoyed much use in the past is described in U.S. Pat. No. 4,497,325 to Victor J. Wedel, which is hereby incorporated herein by this reference. Another type of needle guide which has found increased use recently is similar to the Instrument Guide manufactured by Advanced Technology Industries of Bothell, Washington. This device is attached to an ultrasound transducer which is enclosed in a protective sterile sheath.

While these needle guides, or variations of them, have been used in the past they do have serious drawbacks when viewed in the light of the AIDS threat. Because of the high product cost, both of the guides are typically reused numerous times on various patients from a broad spectrum of backgrounds. This reuse necessitates sterilization procedures for the guides before each new use. Because of the relatively complicated design of these guides, it is often difficult and time consuming to completely sterilize them.

Consequently, a need exists for improved needle guides which reduce the risk of disease transmissions while concomitantly increase the ease in sterilization procedures for ultrasound transducers and related equipment.

SUMMARY OF THE INVENTION

It is an object of the present invention to reduce the risk of transmission of disease during the use of ultrasound transducers in conjunction with needle guides and needles.

It is a feature of the present invention to use a monolithic needle guide in conjunction with an ultrasound transducer and an associated mounting bracket.

It is an advantage of the present invention to increase the ease of the sterilization procedures for the transducer and associated equipment by utilizing all disposable parts which come into contact with the patient and the needle.

It is another object of the present invention to provide a stable guide during needle insertion.

It is another feature of the present invention to include a relatively small external needle guide, having a relatively small surface area in contact with the patient.

It is another advantage of the present invention to allow the physician's hands to firmly grasp the transducer and attached needle guide while still permitting, the much desired, actual physical contact between the physician and the patient.

It is a further object of the present invention to allow quick release of the needle guide from the transducer.

It is a further feature of the present invention to employ a needle guide, of a somewhat resilient material, having a notch therein for engaging a mounting bracket.

It is a further advantage of the present invention to facilitate quick release of the needle guide from the transducer while not requiring complete removal of the transducer.

The present invention provides a monolithic disposable needle guide for ultrasound transducers designed to satisfy the aforementioned needs, provide the previously propounded objects, include the above-described features and produced the earlier articulated advantages. The invention is "sterilization-less" and "broad-based-less" in the sense that the entire needle guide is not subjected to repeated sterilization procedures in order to reduce the risk of disease transmission from one patient to another and the needle guide does not have a broad base at the interface with the patient. Instead, a single monolithic and disposable needle guide having a small "footprint" is used with a transducer and a mounting bracket.

Accordingly, the present invention utilizes an ultrasound transducer in combination with a mounting bracket thereon and a single quick release monolithic disposable need guide.

DETAILED DESCRIPTION

Figure 1:
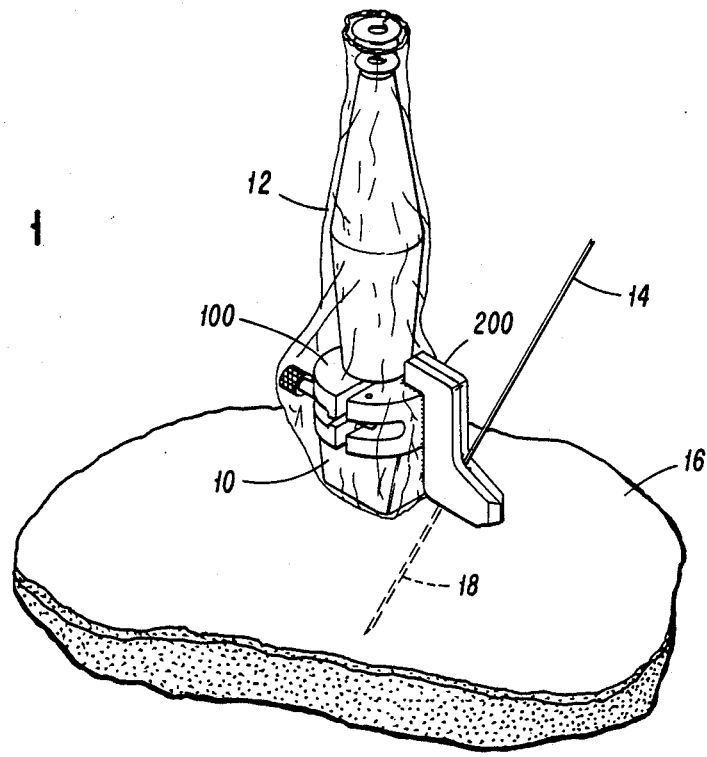
FIG. 1 is a perspective and schematic view of the needle guide and mounting bracket of the present invention together with a needle, ultrasound transducer, and associated sterile sheath in a representative environment.

In the following detailed description, and drawings, it is understood that like reference numerals refer to like objects throughout.

Now, referring to FIG. 1 there is shown, an ultrasound transducer 10, with a mounting bracket, generally designed 100, thereon both of which are disposed within a semi-transparent sheath 12. The needle guide, generally designated 200, is shown attached to the bracket 100 with the sheath 12 interposed therebetween, and is further shown having a needle 14 extending therethrough into a representative patient 16. Dashed lines 18 represent the needle 14 under the surface of the skin of the patient 16. The needle 14 may be substituted with a biopsy instrument, catheter or other medical instrument.

The ultrasound transducer 10, is well known and use in the art, but substitution of an alternative imaging device is contemplated. Similarly, the semitransparent sheath 12 is well known and is used in the art, but anything irrespective of its optical characteristics which serves to isolate the transducer 10 and the bracket 100 from the patient 16, the needle 14 and the needle guide 200 may be substituted.

The configuration of the transducer 10, the needle guide 200, the needle 14 and the patient 16 are such that, a physician can firmly grasp the transducer 10 and needle guide with one hand while still maintaining contact with the patient 16, and manipulate the needle 14 with the other hand. This maintained physician to patient contact is often desired by both doctors and patients alike.

Figure 2:
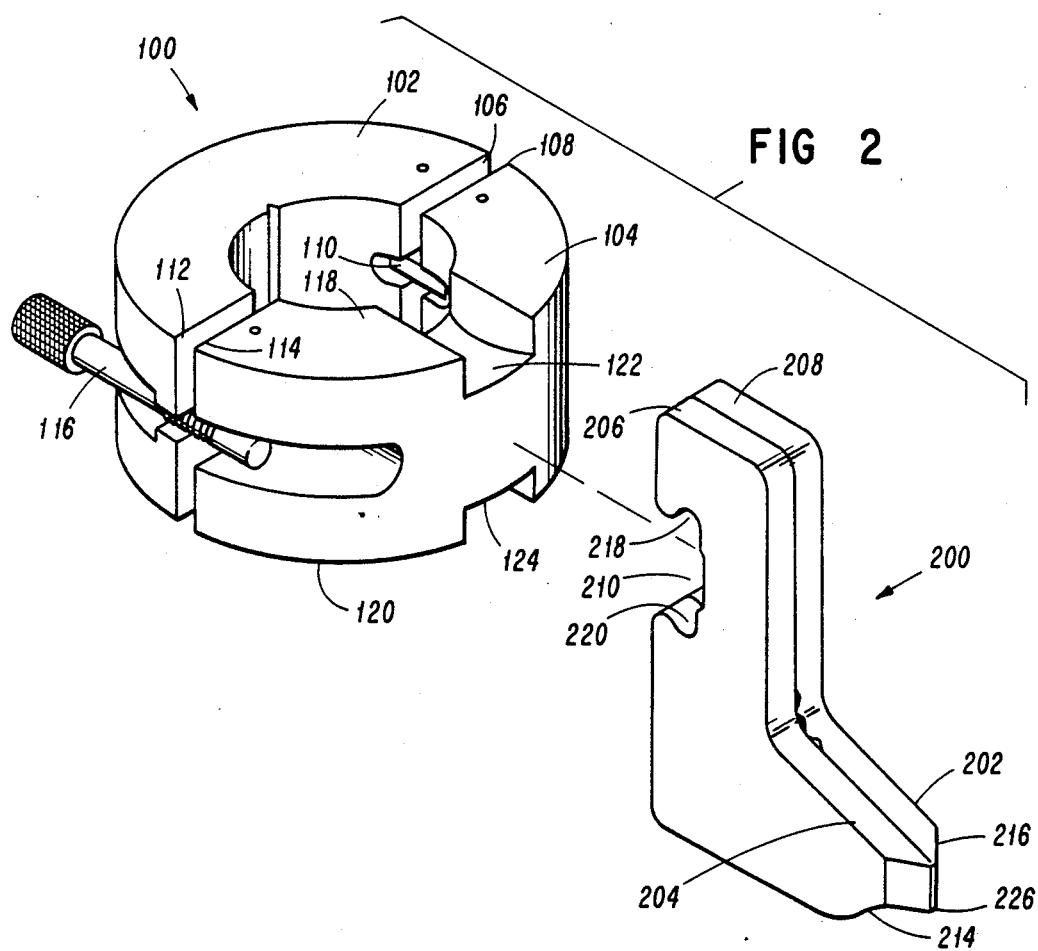
FIG. 2 is an exploded perspective view of the mounting bracket and needle guide of the present invention.

Now referring to FIG. 2, there is shown the mounting bracket 100 together with the needle guide 200. The bracket 100 comprises a first semi-circular and concave member 102 and a second semi-circular and concave member 104. The members 102, and 104 are preferably made of aluminum/lexan plastic. Members 102 and 104 are connected; at a hinge end 106 and 108, respectively, by a hinge 110, and at a latch end 112 and 114, respectively by a latch 116.

Member 104 has a top side 118 and a bottom side 120. A top notch 122, and a bottom notch 124 are present in member 104 at its top side 118 and bottom side 120 respectively. Notches 122, and 124 are for receiving guide 200, with the sheath 12 (FIG. 1) interposed there between.

Guide 200 has a notched side 202 and a smooth side 204. Sides 202 and 204 have a smooth side top end 206, notched side top end 208, a smooth side 210, a notched side notch 212, a smooth side bottom end 214 and a notched side bottom end 216.

Notches 210 and 212 are present so that guide 200 may engage with bracket 100 and are formed with recesses 218, 220, 222, and 224 in order to facilitate a quick release.

Sides 202 and 204 are joined together at a common edge 226, to create a hinged link arrangement which enables the sides 202 and 204 to be separated for needle installation and removal.

Figure 3:
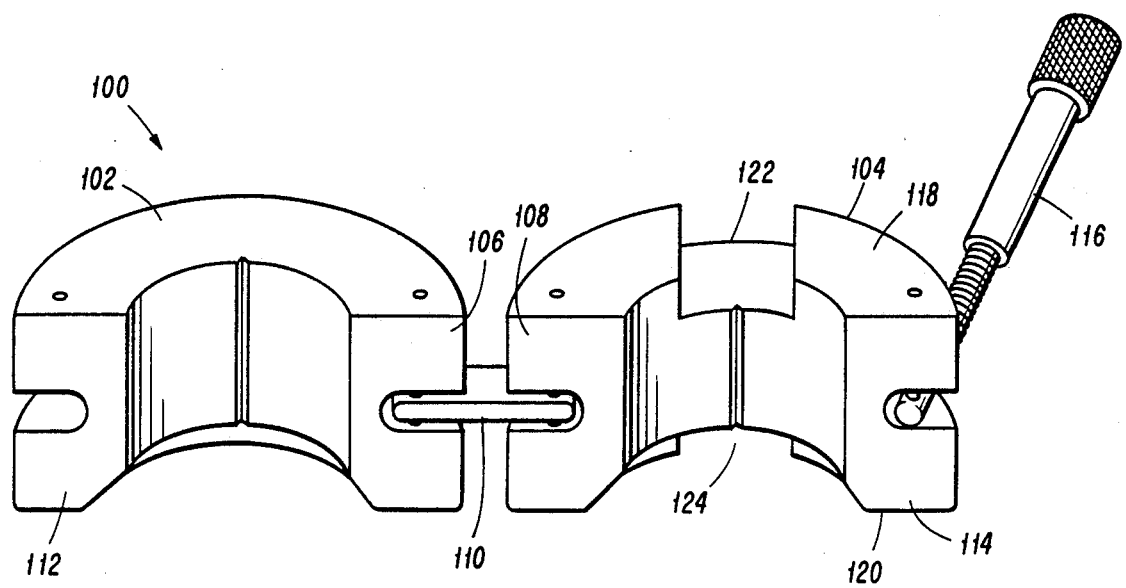
FIG. 3 is a perspective view of the mounting bracket of the present invention in an opened position.

Now referring to FIG. 3, there is shown the mounting bracket generally designated 100, in an open position.

Figure 4:
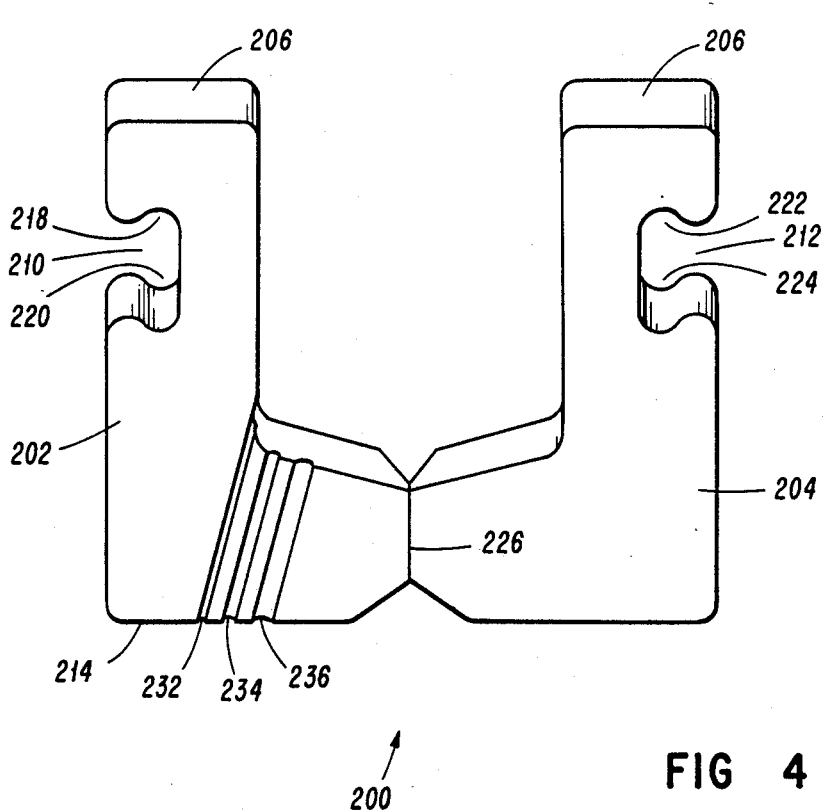
FIG. 4 is a perspective view of the needle guide of the present invention in an opened position.

Now referring to FIG. 4, there is shown the needle guide 200, in an opened position. There is also shown a grooved notched surface 228 and a nongrooved surface 230. Grooved surface 228 contain 3 grooves, 232, 234, and 236. Therein for receiving different sized needles.

It is thought that the monolithic disposable needle guide for ultrasound transducers of the present invention, and many of its attendant advantages, will be understood from the foregoing description, at it will be apparent that various changes may be made in the form, construction, and arrangement of the parts thereof without departing from the spirit and scope of the invention, or sacrificing all of its material advantages, the form herein before described being merely a preferred or exemplary embodiment thereof. It is the intention of the appended claims to cover all of such changes.

I claim:

1. A needle guide for use with an ultrasound transducer in medical procedures, comprising in operative combination:
    (a) a monolithic member having at least one groove therein for receiving a needle;
    (b) a mounting bracket for attachment to the transducer and said mounting bracket having for receiving said monolithic member;
    (c) said monolithic member having a notch therein for cooperating with said bracket;
    (d) said monolithic member further having a first portion, a second portion, and a hinge connecting said first portion with said second portion;
    (e) said first portion having at least one groove therein for receiving a needle;
    (f) said first portion further having a notch therein for receiving said bracket; and
    (g) said second portion further having a notch therein for receiving said bracket.

2. A guide of claim 1 wherein said first and second portions each have a nonrectangular notch therein and said first and second portions having at least one off-center additional recession.

3. A guide of claim 2 where said bracket is formed to receive said member at said notches.

4. A guide of claim 3 wherein said member is made from a resilient material.

5. A medical instrument guide system for use during procedures involving the insertion of a medical instrument into a patient with the aid of an ultrasound scanner comprising in operative combination:
    (a) an ultrasound transducer, for providing an image of the patient;
    (b) a mounting bracket attached to said transducer, said mounting bracket having means to be removably attached to said transducer;
    (c) a sheath disposed about said transducer and said bracket for isolating said transducer and said bracket from the patient;
    (d) a guide member detachably connected to said bracket, with said sheath interposed there between, said guide member for receiving and guiding a medical instrument into a patient;
    (e) said guide member having a first portion having at least one medical instrument receiving groove therein, a second portion attached to said first portion, and a hinge for connecting said first portion and said second portion;
    (f) said first portion and said second portion each having a nonrectangular notch therein for receiving said bracket and said nonrectangular notches allowing for quick release from said bracket; and
    (g) said guide member being composed of a resilient material for allowing the bracket to be quickly and easily detached, whereby the medical instrument is placed within one of said grooves in said first portion, which is then caused to close together about said hinge with said second portion, which are then attached to the sheath enclosed bracket, said bracket being attached to said transducer, so that the medical instrument may be indirectly attached to said transducer and yet being capable of movement through said grooves so as to contact the patient.

* * * * *